US011851631B2

(12) United States Patent
Warr et al.

(10) Patent No.: US 11,851,631 B2
(45) Date of Patent: Dec. 26, 2023

(54) HOUSEHOLD PRODUCT DELIVERING COOLING SENSATIONS

(71) Applicant: TAKASAGO INTERNATIONAL CORPORATION, Tokyo (JP)

(72) Inventors: Jonathan Warr, Paris (FR); Johan Poncelet, Paris (FR); Stuart Fraser, Cheshire (GB)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 909 days.

(21) Appl. No.: 16/078,482

(22) PCT Filed: Feb. 23, 2017

(86) PCT No.: PCT/JP2017/006956
§ 371 (c)(1),
(2) Date: Aug. 21, 2018

(87) PCT Pub. No.: WO2017/146181
PCT Pub. Date: Aug. 31, 2017

(65) Prior Publication Data
US 2021/0179969 A1  Jun. 17, 2021

(30) Foreign Application Priority Data
Feb. 24, 2016  (EP) .................................... 16305215

(51) Int. Cl.
*C11B 9/00* (2006.01)
*A61L 9/00* (2006.01)
(Continued)

(52) U.S. Cl.
CPC .............. *C11B 9/0034* (2013.01); *A61L 9/00* (2013.01); *C11D 3/50* (2013.01); *C11D 11/0023* (2013.01);
(Continued)

(58) Field of Classification Search
CPC ...................................................... C11B 9/0034
See application file for complete search history.

(56) References Cited

U.S. PATENT DOCUMENTS 4,814,212 A    3/1989  Spector
5,773,410 A    6/1998  Yamamoto
(Continued)

FOREIGN PATENT DOCUMENTS

EP    0694514 A2    1/1996
EP    1496095 A1    1/2005
(Continued)

OTHER PUBLICATIONS

Communication dated Mar. 16, 2021 issued by the Japanese Intellectual Property Office in counterpart Japanese Application No. 2018-532332.
(Continued)

*Primary Examiner* — Arrie L Reuther
(74) *Attorney, Agent, or Firm* — Sughrue Mion, PLLC (57) ABSTRACT

A household product contains a fragrance composition, in which the fragrance composition contains from about 0.2 to less than 10% by weight of isopulegol, based on the total weight of the fragrance composition. A method for delivering a perceived cooling sensation in the air includes dispersing isopulegol into the air, or implementing the household product as the above.

14 Claims, 1 Drawing Sheet (51) Int. Cl.
*C11D 3/50* (2006.01)
*C11D 11/00* (2006.01)
*A61L 101/34* (2006.01)
*E03D 9/02* (2006.01)

(52) U.S. Cl.
CPC ............ *A61L 2101/34* (2020.08); *E03D 9/02* (2013.01); *E03D 2009/024* (2013.01)

(56) References Cited

U.S. PATENT DOCUMENTS

| | | | |
|---|---|---|---|
| 6,036,925 | A | 3/2000 | Adams et al. |
| 6,267,297 | B1 | 7/2001 | Contadini et al. |
| 2005/0129721 | A1 | 6/2005 | Ishida et al. |
| 2007/0122373 | A1 | 5/2007 | Woo et al. |
| 2008/0112910 | A1 | 5/2008 | Ishida et al. |
| 2011/0081393 | A1 | 4/2011 | Komatsuki et al. |
| 2013/0131169 | A1 | 5/2013 | Komatsuki et al. |
| 2016/0089464 | A1* | 3/2016 | Frankenbach ....... A61K 8/4926 702/30 |

FOREIGN PATENT DOCUMENTS

| | | |
|---|---|---|
| EP | 2966159 A1 | 1/2016 |
| GB | 1315626 A | 5/1973 |
| JP | 6-11299 B2 | 2/1994 |
| JP | 6-65023 A | 3/1994 |
| JP | 8-40959 A | 2/1996 |
| JP | 2011-21195 A | 2/2011 |
| JP | 2011-79953 A | 4/2011 |
| WO | 97/04993 A1 | 2/1997 |
| WO | 97/34993 A1 | 9/1997 |
| WO | 03/074622 A1 | 9/2003 |
| WO | 2006/102052 A2 | 9/2006 |
| WO | 2015/062997 A1 | 5/2015 |

OTHER PUBLICATIONS

Communication dated Apr. 6, 2021, issued by Ministry of Law and Human Rights of the Republic of Indonesia Directorate General of Intellectual Property in Indonesian Application No. PID201806295.
Leffingwell, J., "Cooling Ingredients and Their Mechanism of Action", 2009, Handbook of Cosmetic Science and Technology, 3rd Edition, 15 pages total.
Sell, C., "Terpenoids", Sep. 2006, Kirk-Othmer Encyclopedia of Chemical Technology, John Wiley & Sons, Inc., 143 pages total, XP 055045533.
Dewis, et al., "Molecules of Taste and Sensation", Jan. 2005, Chemistry and Technology of Flavors and Fragrances, John Wiley & Sons, 45 pages total, XP 002602324.
Search Report dated Dec. 19, 2017, issued by the International Searching Authority in counterpart International Patent Application No. PCT/JP2017/006956 (PCT/ISA/210).
Written Opinion dated Dec. 19, 2017, issued by the International Searching Authority in counterpart International Patent Application No. PCT/JP2017/006956 (PCT/ISA/237).

* cited by examiner

HOUSEHOLD PRODUCT DELIVERING COOLING SENSATIONS

TECHNICAL FIELD

The present invention relates to a household product comprising a fragrance composition, said fragrance composition comprising isopulegol capable of delivering a perceived cooling sensation in the air, but without the product formulation per se coming into direct contact with the skin or mucous membranes of the subject nor of the product needing to be in close proximity to the nose. In particular, the household product of the invention may be an air freshener dispenser device, a floor cleaner, a toilet rim block, or a toilet cistern block. The invention also relates to a method for delivering a perceived cooling sensation in the air.

BACKGROUND ART

Air care products for reducing or masking malodors in the air in homes and enclosed public buildings are commercially available. S. C. Johnson sells products under the GLADE (registered trademark) brand name, Reckitt-Benckiser sells products under the AIR WICK (registered trademark) brand name, and Procter & Gamble sells products under the FEBREZE (registered trademark) and AMBI PUR (registered trademark) brand names. Air freshener compositions have been widely described in the patent literature, for instance in GB 1 315 626 A (PTL 1); U.S. Pat. No. 6,267,297 B1 (PTL 2); U.S. Pat. No. 4,814,212 A (PTL 3); U.S. Pat. No. 6,036,925 A (PTL 4); and US 2007/0122373 A1 (PTL 5). These products may take several forms as they can be directed devices such as aerosol sprays or trigger sprays which can be applied at the users discretion to specific sites or they can be general air fresheners for a room such as automatic sprays, plug in electrical devices and diffusion devices, such as gels, candles, wax melts or reed diffusers. Another group of vapour-dispensing devices utilizes a carrier material such as paperboard impregnated or coated with a vaporizable composition. Manufacturers are constantly seeking to improve the functionality of these products and add further benefits such as malodour reduction, insect repellency or alternating fragrances to avoid habituation.

Cooling agents are chemical compounds which provide a cooling sensation of the skin and mucous membranes by stimulating the cold receptors of the human body. Cooling agents are well-described in the article "Cooling Ingredients and Their Mechanism of Action", John C. Leffingwell, from the Handbook of Cosmetic Science and Technology, 3$^{rd}$ edition, Andre O. Barel, Marc Paye, Howard I. Maibach, published by Informa Healthcare, New York, 2009 (NPL 1). It is well known to add cooling agents to consumer products to enhance the sensory experience. Typical examples of such products are edible and potable compositions, such as:
- beverages, confectionery and chewing gums;
- toiletries such as after-shave lotions, shaving creams, gels and foams, deodorants and antiperspirants, toilet soaps, bath oils and salts, shampoos, hair conditioners, body washes, lipsticks, hair oils, talcum powders, face creams, hand creams, sun-burn lotions, cleansing tissues, dentifrices, and mouthwashes;
- medicinal products and allied compositions including antiseptic ointments, liniments, lotions, decongestants, cough mixtures, throat lozenges, indigestion preparations and oral analgesics.

CITATION LIST

Patent Literature

PTL 1: GB 1 315 626 A
PTL 2: U.S. Pat. No. 6,267,297 B1
PTL 3: U.S. Pat. No. 4,814,212 A
PTL 4: U.S. Pat. No. 6,036,925 A
PTL 5: US 2007/0122373 A1

Non Patent Literature

NPL 1: "Cooling Ingredients and Their Mechanism of Action", John C. Leffingwell, from the Handbook of Cosmetic Science and Technology, 3rd edition, Andre O. Barel, Marc Paye, Howard I. Maibach, published by Informa Healthcare, New York, 2009.

SUMMARY OF INVENTION

Technical Problem

Typical examples of the cooling agents are L-menthol, camphor, methyl salicylate, borneol, cineole, menthone, spearmint oil, peppermint oil, 3-(L-menthoxy)propane-1,2-diol, paramenthane-3,8-diol, menthyl 3-hydroxybutyrate, cubebol, n-ethyl-p-menthane-3-carboxamide (WS-3), 2-isopropyl-N,2,3-trimethylbutyramide (WS-23), L-menthone 1,2-glycerol ketal, menthyl lactate, menthyl succinate, and menthyl acetate. However, these cooling agents require to be applied directly to the skin or to be used in close proximity to the skin. Another drawback is that many of these cooling agents have strong odours which may not be entirely pleasant and which may not always blend harmoniously with other fragrance notes. For instance, menthol has been one of the predominant cooling "sensate" agents, but consumers sometimes consider its note inappropriate for many fragrance and flavour applications as they prefer a cooling sensation divorced from the mint odour of menthol and other odorous "sensate" compounds.

Solution to Problem

The present invention provides a household product comprising a fragrance composition based on a cooling agent significantly less intense than menthol, namely isopulegol, which is sufficiently volatile so as to evaporate with the fragrance and deliver perceived cooling sensation in air. It has indeed been found that when isopulegol is formulated into a fragrance composition, a person smelling the composition perceives the air to be cooler/fresher. Household products comprising such a fragrance composition will therefore provide a benefit to consumers. In the context of the present invention, the household product is a non-ingested and a non-topically applied product. Further to avoid being restricted to a narrow range of fragrance notes due to the odour of the cooling agent itself, isopulegol is less intense than menthol so it can be used at high dosages in a wide range of fragrance compositions with little impact on the fragrance note of the composition.

Accordingly, in a first aspect, the invention relates to a household product comprising a fragrance composition, in which said fragrance composition comprises from about 0.2 to less than 10% by weight of isopulegol, based on the total weight of the fragrance composition.

The household product may be an air freshener dispenser device, a floor cleaner, a kitchen or bathroom surface cleaner, a toilet rim block, or a toilet cistern block, each comprising such a fragrance composition.

The invention also relates to the use of isopulegol or of the household product according to the invention, as an agent for delivering a perceived cooling sensation in the air.

Finally, the invention relates to a method for delivering a perceived cooling sensation in the air by dispersing isopulegol into the air, or implementing the household product according to the invention, such as an air freshener dispenser device, a floor cleaner, a kitchen or bathroom surface cleaner, a toilet rim block, or a toilet cistern block.

Advantageous Effects of Invention

In the present invention, it is possible to deliver a perceived cooling sensation in the air, but without the product formulation per se coming into direct contact with the skin or mucous membranes of the subject nor of the product needing to be in close proximity to the nose.

DESCRIPTION OF EMBODIMENTS

According to a first aspect, the invention relates to a household product comprising a fragrance composition, said fragrance composition comprising from about 0.2 to less than 10% by weight of isopulegol, preferably (−)-isopulegol, based on the total weight of the fragrance composition.

Isopulegol is known as a cooling agent that provides a cooling effect to the skin by directly stimulating the receptors of the nerve endings of the skin to produce a cooling sensation. The Inventors have now surprisingly discovered that isopulegol also produces a perceived cooling sensation in the air and can be used in household products containing a fragrance composition, without affecting the fragrance note of the fragrance composition. The Inventors have observed that isopulegol affects the trigeminal nerve (a nerve responsible for sensation in the face, nose, and mouth, including pain, temperature and touch) and induces a trigeminal response of the brain. Isopulegol thus emerges as being a trigeminal-stimulating compound.

The household product of the invention advantageously comprises a fragrance composition comprising from about 0.2 to about 9 wt %, about 0.2 to about 8 wt %, about 0.2 to about 7 wt %, about 0.2 to about 6 wt %, about 0.2 to about 5 wt %, about 0.2 to about 4 wt %, or about 0.2 to about 3 wt % of isopulegol, based on the total weight of the fragrance composition. The fragrance composition may comprise from about 1 to about 9 wt %, about 1 to about 8 wt %, about 1 to about 7 wt %, about 1 to about 6 wt %, about 1 to about 5 wt %, about 1 to about 4 wt % or about 1 to about 3 wt % of isopulegol, based on the total weight of the fragrance composition. The fragrance composition may also comprise from about 2 to about 9 wt %, about 2 to about 8 wt %, about 2 to about 7 wt %, about 2 to about 6 wt %, about 2 to about 5 wt %, or about 2 to about 4 wt % of isopulegol, based on the total weight of the fragrance composition.

Isopulegol is available either as a racemic mixture (CAS 7786-67-6), or as the (−)-isomer (CAS 89-79-2). In one embodiment isopulegol is available as Coolact (registered trademark) P, a product from Takasago. The isopulegol of the invention may have an optical isomer and chemical purity of greater than 90%, preferably greater than 95%, more preferably greater than 97.5%, and even more preferably greater than 99%. Isopulegol purity is determined by gas chromatography using the method described in U.S. Pat. No. 5,773,410 by summing the area percent of impurity peaks and subtracting these from the total measured area which is taken to be 100%.

In one embodiment, the household product comprises a fragrance composition which further comprises one or more cooling agents, preferably incorporated, in total of the cooling agents, in an amount of from about 0.1 to about 10% by weight, preferably from about 0.1 to about 5% by weight, more preferably from about 0.1 to about 2.5% by weight, based on the total weight of the fragrance composition. The other cooling agent is advantageously selected from the group consisting of: menthol (CAS 89-78-1), menthone (CAS 14073-97-3), menthyl acetate (CAS 79-20-9), menthyl lactate (CAS 547-64-8), camphor (CAS 76-22-2), 1,4-cineole (CAS 470-82-6), p-menthane-3,8-diol (CAS 42822-86-6), menthoxypropanediol (CAS 87061-04-9), menthone glycerin acetal (CAS 63187-91-7), 2-isopropyl-5-methylcyclohexyl-3-hydroxybutanoate (CAS 108766-16-1), N-ethyl-5-methyl-2-(1-methylethyl)cyclohexanecarboxamide (CAS 39711-79-0), N,2,3-trimethyl-2-propan-2-ylbutanamide (CAS 51115-67-4), (3S,3aR,3bR,4S,7R,7aR)-3,7-dimethyl-4-(propan-2-yl)octahydro-1H-cyclopenta[1,3]cyclopropa[1,2]benzen-3-ol (CAS 23445-02-5), spearmint oil (CAS 8008-79-5) and peppermint oil (CAS 8006-90-4). It may be preferred that, when the other cooling agent is menthol (CAS 89-78-1), camphor (CAS 76-22-2), cineole (CAS 470-82-6), spearmint oil (CAS 8008-79-5) or peppermint oil (CAS 8006-90-4), its amount does not exceed 2.5% by weight of the total weight of the fragrance composition.

According to another embodiment, the household product comprises a fragrance composition, which further comprises a perfume ingredient, and preferably at least two, such as at least five, or at least eight distinct perfume ingredients. It can comprise highly complex mixtures of perfume ingredients, chosen to provide any desired odour. Perfume ingredients typically used in the field of perfumery and suitable for the purposes of the present invention are described more fully in S. Arctander, Perfume Flavors and Chemicals 1969, Vols. I and II, Montclair, N. J. and in The Merck Index, $8^{th}$ edition, Merck & Co., Inc. Rahway, N. J. The term "perfume ingredient" encompasses naturally occurring as well as synthetic perfume materials known for use in perfumes, as well as animal oils. A perfume ingredient can also be any natural oil or extract, or chemical compound used in a fragrance composition. Natural oils and extracts are described in The Essential Oils by E Guenther published in 1949 by Van Nostrand and may include extracts, pressings, collection of exudates, and distillates from any part of suitable plants: roots, rhizomes, bulbs, corms, stem, bark, heartwood, leaves, flowers, seeds and fruit. Examples of such extracts and distillates include citrus fruit oils such as orange, mandarin, grapefruit, lime or lemon oils, tree oils such as pine, or cedarwood, herb oils such as peppermint, thyme, lavender, basil, rosemary, clove or flower extracts such as rose, jasmine, muguet, or geranium oil.

It may be preferred that each perfume ingredient has a molecular weight greater than 100 g/mol, preferably greater than 120 g/mol and lower than 325 g/mol, preferably lower than 300 g/mol. It may further be preferred that each perfume ingredient has a boiling point in the range 80-400° C., such as in the range 100-350° C., when measured at 760 mm Hg.

Advantageously, the perfume ingredient is selected from the following list.

$C_8$-$C_{18}$ hydrocarbons, preferably delta-3-carene, alpha-pinene, beta-pinene, alpha-terpinene, gamma-terpinene, p-cymene, bisabolene, camphene, caryophyllene, cedrene, farnesene, limonene, longifolene, myrcene, ocimene, valencene, and (E,Z)-1,3,5-undecatriene.

$C_2$-$C_{18}$ aliphatic alcohols, preferably hexanol, octanol, 3-octanol, 2,6-dimethylheptanol, 2-methylheptanol, 2-methyloctanol, (E)-3-hexenol, (E) and (Z)-3-hexenol, 1-octen-3-ol, mixtures of 3,4,5,6,6-pentamethyl-3/4-hepten-2-ol and 3,5,6,6-tetramethyl-4-methyleneheptan-2-ol, (E,Z)-2,6-nonadienol, 3,7-dimethyl-7-methoxyoctan-2-ol, 9-decenol, 10-undecenol, and 4-methyl-3-decen-5-ol.

$C_2$-$C_{18}$ aliphatic aldehydes and their acetals, preferably hexanal, heptanal, octanal, nonanal, decanal, undecanal, dodecanal, tridecanal, 2-methyloctanal, 2-methylnonanal, (E)-2-hexenal, (Z)-4-heptenal, 2,6-dimethyl-5-heptenal, 10-undecenal, (E)-4-decenal, 2-dodecenal, 2,6,10-trimethyl-5,9-undecadienal, heptanal diethyl acetal, 1,1-dimethoxy-2,2,5-trimethyl-4-hexene, and citronellyl oxyacetaldehyde.

$C_3$-$C_{18}$ aliphatic ketones and oximes thereof, preferably 2-heptanone, 2-octanone, 3-octanone, 2-nonanone, 5-methyl-3-heptanone, 5-methyl-3-heptanone oxime, and 2,4,4,7-tetramethyl-6-octen-3-one.

$C_2$-$C_{18}$ aliphatic sulphur-containing compounds, preferably 3-methylthiohexanol, 3-methylthiohexyl acetate, 3-mercaptohexanol, 3-mercaptohexyl acetate, 3-mercaptohexyl butyrate, 3-acetylthiohexyl acetate, and 1-menthene-8-thiol.

$C_2$-$C_{18}$ aliphatic nitrile-containing compounds, preferably 2-nonenenitrile, 2-tridecenenenitrile, 2,12-tridecenene-nitrile, 3,7-dimethyl-2,6-octadienenitrile, and 3,7-dimethyl-6-octenenitrile.

$C_2$-$C_{18}$ aliphatic carboxylic acids and esters thereof, preferably (E)- and (Z)-3-hexenyl formate, ethyl acetoacetate, isoamyl acetate, hexyl acetate, 3,5,5-trimethylhexyl acetate, 3-methyl-2-butenyl acetate, (E)-2-hexenyl acetate, (E)- and (Z)-3-hexenyl acetate, octyl acetate, 3-octyl acetate, 1-octen-3-yl acetate, ethyl butyrate, butyl butyrate, isoamyl butyrate, hexyl butyrate, (E)- and (Z)-3-hexenyl isobutyrate, hexyl crotonate, ethyl isovalerate, ethyl 2-methylpentanoate, ethyl hexanoate, allyl hexanoate, ethyl heptanoate, allyl heptanoate, ethyl octanoate, ethyl (E,Z)-2,4-decadienoate, methyl 2-octynoate, methyl 2-nonynoate, allyl-2-isoamyloxy acetate, and methyl-3,7-dimethyl-2,6-octadienoate.

$C_4$-$C_j$ acyclic terpene alcohols, preferably citronellol, geraniol, nerol, linalool, lavandulol, nerolidol, farnesol, tetrahydrolinalool, tetrahydrogeraniol, 2,6-dimethyl-7-octen-2-ol, 2,6-dimethyloctan-2-ol, 2-methyl-6-methylene-7-octen-2-ol, 2,6-dimethyl-5,7-octadien-2-ol, 2,6-dimethyl-3,5-octadien-2-ol, 3,7-dimethyl-4,6-octadien-3-ol, 3,7-dimethyl-1,5,7-octatrien-3-ol, and 2,6-dimethyl-2,5,7-octatrien-1-ol.

$C_4$-$C_{18}$ acyclic terpene aldehydes and ketones, preferably geranial, neral, citronellal, 7-hydroxy-3,7-dimethyloctanal, 7-methoxy-3,7-dimethyloctanal, 2,6,10-trimethyl-9-undecenal, geranylacetone, and the dimethyl and diethyl acetals of geranial, neral, and 7-hydroxy-3,7-dimethyloctanal.

$C_4$-$C_{18}$ cyclic terpene alcohols, preferably alpha-terpineol, terpineol-4, menthan-8-ol, menthan-1-ol, menthan-7-ol, borneol, isoborneol, linalool oxide, nopol, cedrol, ambrinol, vetiverol, and guaiol.

$C_4$-$C_{18}$ cyclic terpene aldehydes and ketones, preferably fenchone, alpha-ionone, beta-ionone, alpha-n-methylionone, beta-n-methylionone, alpha-isomethylionone, beta-isomethylionone, alpha-irone, alpha-damascone, beta-damascone, beta-damascenone, delta-damascone, gamma-damascone, 1-(2,4,4-trimethyl-2-cyclohexen-1-yl)-2-buten-1-one, 1,3,4,6,7,8a-hexahydro-1,1,5,5-tetramethyl-2H-2,4a-methanonaphthalen-8(5H)-one, nootkatone, dihydronootkatone, alpha-sinensal, beta-sinensal, and methyl cedryl ketone.

$C_4$-$C_{18}$ cyclic alcohols, preferably 4-tert-butylcyclohexanol, 3,3,5-trimethylcyclohexanol, 3-isocamphylcyclohexanol, 2,6,9-trimethyl-Z2,Z5,E9-cyclododecatrien-1-ol, and 2-isobutyl-4-methyltetrahydro-2H-pyran-4-ol.

$C_4$-$C_{18}$ cycloaliphatic alcohols, preferably alpha-3,3-trimethylcyclohexylmethanol, 2-methyl-4-(2,2,3-trimethyl-3-cyclopent-1-yl)butanol, 2-methyl-4-(2,2,3-trimethyl-3-cyclopent-1-yl)-2-buten-1-ol, 2-ethyl-4-(2,2,3-trimethyl-3-cyclopent-1-yl)-2-buten-1-ol, 3-methyl-5-(2,2,3-trimethyl-3-cyclopent-1-yl)-pentan-2-ol, 3-methyl-5-(2,2,3-trimethyl-3-cyclopent-1-yl)-4-penten-2-ol, 3,3-dimethyl-5-(2,2,3-trimethyl-3-cyclopent-1-yl)-4-penten-2-ol, 1-(2,2,6-trimethylcyclohexyl)pentan-3-ol, and 1-(2,2,6-trimethylcyclohexyl)hexan-3-ol.

$C_4$-$C_{18}$ cyclic and cycloaliphatic ethers, preferably cedryl methyl ether, cyclododecyl methyl ether, (ethoxymethoxy) cyclododecane, alpha-cedrene epoxide, 3a,6,6,9a-tetramethyl-dodecahydronaphtho[2,1-b]furan, 3a-ethyl-6,6,9a-trimethyldodecahydro-naphtho[2,1-b]furan, 1,5,9-trimethyl-13-oxabicyclo[10.1.0]trideca-4,8-diene, rose oxide, and 2-(2,4-dimethyl-3-cyclohexen-1-yl)-5-methyl-5-(1-methylpropyl)-1,3-dioxane.

$C_4$-$C_{18}$ cyclic ketones, preferably 4-tert-butylcyclohexanone, 2,2,5-trimethyl-5-pentylcyclopentanone, 2-heptylcyclopentanone, 2-pentylcyclopentanone, 2-hydroxy-3-methyl-2-cyclopenten-1-one, 3-methyl-cis-2-penten-1-yl-2-cyclopenten-1-one, 3-methyl-2-pentyl-2-cyclopenten-1-one, 3-methyl-4-cyclopentadecenone, 3-methyl-5-cyclopentadecenone, 3-methylcyclopentadecanone, 4-(1-ethoxyvinyl)-3,3,5,5-tetramethylcyclohexanone, 4-tert-pentylcyclohexanone, 5-cyclohexadecen-1-one, 6,7-dihydro-1,1,2,3,3-pentamethyl-4(5H)-indanone, 9-cycloheptadecen-1-one, cyclopentadecanone, and cyclohexadecanone.

$C_4$-$C_{18}$ cycloaliphatic aldehydes, preferably 2,4-dimethyl-3-cyclohexenecarbaldehyde, 2-methyl-4-(2,2,6-trimethyl-cyclohexen-1-yl)-2-butenal, 4-(4-hydroxy-4-methylpentyl)-3-cyclohexenecarbaldehyde, and 4-(4-methyl-3-penten-1-yl)-3-cyclohexenecarbaldehyde.

$C_4$-$C_{18}$ cycloaliphatic ketones, preferably 1-(3,3-dimethylcyclohexyl)-4-penten-1-one, 1-(5,5-dimethyl-1-cyclohexen-1-yl)-4-penten-1-one, 2,3,8,8-tetramethyl-1,2,3,4,5,6,7,8-octahydro-2-naphthalenyl methyl ketone, methyl-2,6,10-trimethyl-2,5,9-cyclododecatrienyl ketone, and tert-butyl (2,4-dimethyl-3-cyclohexen-1-yl)ketone.

Esters of cyclic alcohols in $C_4$-$C_{18}$, preferably 2-tert-butylcyclohexyl acetate, 4-tert-butyl-cyclohexyl acetate, 2-tert-pentylcyclohexyl acetate, 4-tert-pentylcyclohexyl acetate, decahydro-2-naphthyl acetate, 3-pentyltetrahydro-2H-pyran-4-yl acetate, decahydro-2,5,5,8a-tetramethyl-2-naphthyl acetate, 4,7-methano-3a,4,5,6,7,7a-hexahydro-5 or 6-indenyl acetate, 4,7-methano-3a,4,5,6,7,7a-hexahydro-5 or 6-indenyl propionate, 4,7-methano-3a,4,5,6,7,7a-hexahydro-5 or 6-indenyl isobutyrate, and 4,7-methanooctahydro-5 or 6-indenyl acetate.

Esters of cycloaliphatic carboxylic acids in $C_4$-$C_{18}$, preferably allyl 3-cyclohexylpropionate, allyl cyclohexyloxyacetate, methyl dihydrojasmonate, methyl jasmonate, methyl 2-hexyl-3-oxocyclopentanecarboxylate, ethyl 2-ethyl-6,6-dimethyl-2-cyclohexenecarboxylate, ethyl 2,3,6,6-tetramethyl-2-cyclohexenecarboxylate, and ethyl 2-methyl-1,3-dioxolane-2-acetate.

$C_4$-$C_{18}$ aromatic hydrocarbons, preferably styrene and diphenylmethane.

$C_4$-$C_{18}$ araliphatic alcohols, preferably benzyl alcohol, 1-phenylethyl alcohol, 2-phenylethyl alcohol, 3-phenylpropanol, 2-phenylpropanol, 2-phenoxyethanol, 2,2-dimethyl-3-phenylpropanol, 2,2-dimethyl-3-(3-methylphenyl)propanol, 1,1-dimethyl-2-phenylethyl alcohol, 1,1-dimethyl-3-phenylpropanol, 1-ethyl-1-methyl-3-phenylpropanol, 2-methyl-5-phenylpentanol, 3-methyl-5-phenylpentanol, 3-phenyl-2-propen-1-ol, 4-methoxybenzyl alcohol, and 1-(4-isopropylphenyl)ethanol.

Esters of araliphatic alcohols in $C_4$-$C_{18}$ and aliphatic carboxylic acids in $C_4$-$C_{18}$, preferably benzyl acetate, benzyl propionate, benzyl isobutyrate, benzyl isovalerate, 2-phenylethyl acetate, 2-phenylethyl propionate, 2-phenylethyl isobutyrate, 2-phenylethyl isovalerate, 1-phenylethyl acetate, alpha-trichloromethylbenzyl acetate, alpha,alpha-dimethylphenylethyl acetate, alpha,alpha-dimethylphenylethyl butyrate, cinnamyl acetate, 2-phenoxyethyl isobutyrate, and 4-methoxybenzyl acetate.

$C_2$-$C_{18}$ araliphatic ethers, preferably 2-phenylethyl methyl ether, 2-phenylethyl isoamyl ether, 2-phenylethyl 1-ethoxyethyl ether, phenylacetaldehyde dimethyl acetal, phenylacetaldehyde diethyl acetal, hydratropaldehyde dimethyl acetal, phenylacetaldehyde glycerol acetal, 2,4,6-trimethyl-4-phenyl-1,3-dioxane, 4,4a,5,9b-tetrahydroindeno[1,2-d]-m-dioxin, and 4,4a,5,9b-tetrahydro-2,4-dimethylindeno[1,2-d]-m-dioxin.

$C_4$-$C_{18}$ aromatic and araliphatic aldehydes, preferably benzaldehyde, phenylacetaldehyde, 3-phenylpropanal, hydratropaldehyde, 4-methylbenzaldehyde, 4-methylphenylacetaldehyde, 3-(4-ethylphenyl)-2,2-dimethylpropanal, 2-methyl-3-(4-isopropylphenyl)propanal, 2-methyl-3-(4-tert-butylphenyl)propanal, 3-(4-tert-butylphenyl)propanal, cinnamaldehyde, alpha-butylcinnamaldehyde, alpha-amylcinnamaldehyde, alpha-hexylcinnamaldehyde, 3-methyl-5-phenylpentanal, 4-methoxybenzaldehyde, 4-hydroxy-3-methoxybenzaldehyde, 4-hydroxy-3-ethoxybenzaldehyde, 3,4-methylenedioxybenzaldehyde, 3,4-dimethoxybenzaldehyde, 2-methyl-3-(4-methoxyphenyl)propanal, and 2-methyl-3-(4-methylenedioxyphenyl)propanal.

$C_4$-$C_{18}$ aromatic and araliphatic ketones, preferably acetophenone, 4-methylacetophenone, 4-methoxyacetophenone, 4-tert-butyl-2,6-dimethylacetophenone, 4-phenyl-2-butanone, 4-(4-hydroxyphenyl)-2-butanone, 1-(2-naphthalenyl)ethanone, benzophenone, 1,1,2,3,3,6-hexamethyl-5-indanyl methyl ketone, 6-tert-butyl-1,1-dimethyl-4-indanyl methyl ketone, 1-[2,3-dihydro-1,1,2,6-tetramethyl-3-(1-methylethyl)-1H-5-indenyl]ethanone, and 5',6',7',8'-tetrahydro-3',5',5',6',8',8'-hexamethyl-2-acetonaphthone.

$C_4$-$C_{18}$ aromatic and araliphatic carboxylic acids and esters thereof, preferably phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl salicylate, isoamyl salicylate, hexyl salicylate, cyclohexyl salicylate, cis-3-hexenyl salicylate, benzyl salicylate, phenylethyl salicylate, methyl 2,4-dihydroxy-3,6-dimethylbenzoate, ethyl 3-phenylglycidate, and ethyl 3-methyl-3-phenylglycidate.

Nitrogen-containing aromatic compounds in $C_4$-$C_{18}$, preferably 2,4,6-trinitro-1,3-dimethyl-5-tert-butylbenzene, 3,5-dinitro-2,6-dimethyl-4-tert-butylacetophenone, cinnamonitrile, 5-phenyl-3-methyl-2-pentenenitrile, 5-phenyl-3-methylpentanenitrile, methyl anthranilate, methyl N-methylanthranilate, Schiff bases of methyl anthranilate with 7-hydroxy-3,7-dimethyloctanal, 2-methyl-3-(4-tert-butylphenyl)propanal, 2,4-dimethyl-3-cyclohexene-carbaldehyde, 6-isopropylquinoline, 6-isobutylquinoline, 6-sec-butylquinoline, indole, skatole, 2-methoxy-3-isopropylpyrazine, and 2-isobutyl-3-methoxypyrazine.

Phenols, phenyl ethers and phenyl esters, preferably estragole, anethole, eugenol, eugenyl methyl ether, isoeugenol, isoeugenyl methyl ether, thymol, carvacrol, diphenyl ether, beta-naphthyl methyl ether, beta-naphthyl ethyl ether, beta-naphthyl isobutyl ether, 1,4-dimethoxybenzene, eugenyl acetate, 2-methoxy-4-methylphenol, 2-ethoxy-5-(1-propenyl)phenol, and p-cresyl phenylacetate.

Heterocyclic compounds in $C_4$-$C_{12}$, preferably 2,5-dimethyl-4-hydroxy-2H-furan-3-one, 2-ethyl-4-hydroxy-5-methyl-2H-furan-3-one, 3-hydroxy-2-methyl-4H-pyran-4-one, and 2-ethyl-3-hydroxy-4H-pyran-4-one.

Lactones in $C_4$-$C_{18}$, preferably 1,4-octanolide, 3-methyl-1,4-octanolide, 1,4-nonanolide, 1,4-decanolide, 8-decen-1,4-olide, 1,4-undecanolide, 1,4-dodecanolide, 1,5-decanolide, 1,5-dodecanolide, 1,15-pentadecanolide, cis and trans-1-pentadecen-1,15-olide, cis- and trans-2-pentadecen-1,15-olide, 1,16-hexadecanolide, 9-hexadecen-1,16-olide, 10-oxa-1,16-hexadecanolide, 11-oxa-1,16-hexadecanolide, 12-oxa-1,16-hexadecanolide, ethylene 1,12-dodecanedioate, ethylene 1,13-tridecanedioate, coumarin, 2,3-dihydrocoumarin, and octahydrocoumarin.

The perfume ingredient present in the fragrance composition of the household product preferably does not contain ionizing functional groups, such as sulfonates, sulphates, phosphates or quaternary ammonium ions.

The fragrance compositions of the invention may include one or more support materials, such as solvents or UV stabilizers. The amount of solvent(s) may represent up to 60% by weight, such as up to 50% by weight, such as up to 40% by weight, of the total weight of the household product. Examples of suitable solvents include hydrocarbons such as those sold under the trade name Isopar (registered trademark); ethers such as those sold under the trade name Dowanol (registered trademark); benzyl benzoate; isopropyl myristate; dialkyl adipates; dialkyl succinates; dialkyl glutarates, such as the dimethyl esters sold under the trade name Flexisolv (registered trademark); citrate esters, such as triethyl citrate and acetyl tributyl citrate; soybean methyl ester such as ME-S1885 (sold by Peter Cremer NA); diethyl phthalate; diethylene glycol monoethyl ether; 3-methoxy-3-methyl-1-butanol; dipropylene glycol; and iso-propylidene glycerol sold under the trade name Augeo™ Clean Multi. Examples of UV stabilisers include butyl methoxy dibenzoyl methane; bis ethylhexyloxyphenol-methoxyphenyl triazine; and those sold under the trade name Uvinul (registered trademark) such as Uvinul (registered trademark) D50 [bis(2,4-dihydroxyphenyl)-methanone], Uvinul (registered trademark) MC80 (octyl methoxycinnamate) and Uvinul (registered trademark) M40 (benzophenone 3).

In one embodiment, the household product of the invention is an air freshener dispenser device.

The air freshener dispenser device can be:

a passive evaporative device selected from sprayers (such as automatic sprays, hand operated pressurised aerosol sprays or pump action sprays, as illustrated in US 2007/0122373), diffusers, gels, candles, waxes, wax melts, pot-pourri, impregnated papers and laminated cardboard, or an electrically powered air freshener dispenser device, preferably comprising a heating element, said electrically powered air freshener dispenser device being preferably a piezo-electric device or a plug, for example as described in U.S. Pat. No. 6,123,935.

According to another embodiment, the household product of the invention is a kitchen or bathroom surface cleaner or a floor cleaner. Floor cleaners, also known as general purpose cleaner, also include carpet cleaner. They may be in several forms: isotropic liquids, thickened liquids with or without abrasive, pastes, gels, foams or sprays. They can be used directly from the bottle or after dilution in water. Various delivery methods have been devised for the convenience of the users, some are sprayed onto surfaces from trigger spray bottles, or alternatively they can be poured directly onto surfaces. They may contain additional ingredients such as acids for limescale removal, biocides for hygiene, or bleaching agents. A standard floor cleaner composition is given in Table 1 below, which summarises the main ingredients and their quantities (taken from Surfactant Science Series Vol. 67 Liquid Detergents chapter on Speciality Liquid Household Surface Cleaners p. 479, Table 4).

TABLE 1

Standard floor cleaner composition

| Ingredients | Example | Amount wt % |
|---|---|---|
| Anionic surfactant | Alkylbenzene sulfonate as supplied by Shell as Dobs 055, alkane sulphonate as Hostaspur SAS60 | 0-35 |
| Nonionic surfactant | Ethoxylated alcohol as Neodol 9-11 6EO, mixed ethoxy/propoxy alcohol as the Pluronic (registered trademark) series from BASF, amine oxide, alkanolamides and betaines | 1-35 |
| Hydrotropes | Sodium cumene sulphonate, xylene sulphonate | 0-10 |
| Builder/sequestrant | Citrates, EDTA salts, phosphonate salts, lactic acid and polyacrylates | 0-10 |
| Solvent | Lower alcohols, glycol ethers, benzyl alcohol, hydrocarbons such as limonene | 0.5-50 |
| Disinfectant | Hypochlorite bleach, pine oil, alcohols in $C_1$-$C_6$, quaternary ammonium salts | 0-15 |
| Perfume, colour, thickening polymer, sequestrant, preservatives | — | 0.1-3 |
| Water | — | up to 100 |

According to another embodiment, the household product of the invention is a solid or liquid toilet rim block.

Solid toilet rim blocks are intended to be located under the rim of a lavatory bowl or urinal such that, during a flushing cycle, water from the cistern flows over the block thereby dissolving a portion of the toilet rim block. The invention also relates to cageless rim blocks which adhere directly to the surface of the lavatory pan, and to solid toilet cistern blocks which are placed in the cistern and dissolve slowly in the water contained therein. It will be appreciated that the solubility characteristics of these two products are quite different, since one is constantly under water while the other has intermittent short term contact with water. However, they both contain a surfactant, fillers, and a fragrance composition as defined according to the invention, and optionally bleaching agents, germicides and anti-limescale agents. Typical formulations are described in EP 0 462 643, GB 2 178 442, U.S. Pat. Nos. 4,874,536 and 8,658,588, which are incorporated herein by reference.

Liquid toilet rim blocks are devices that dispense liquid compositions directly into a lavatory bowl from under the rim of said bowl. Such liquid toilet rim blocks are usually attached by various means, such as hooks and the like, to the rim of the lavatory bowl. Every time a toilet equipped with a liquid toilet rim block is flushed, an amount of composition is dispensed into the lavatory bowl. Examples of liquid toilet rim blocks are given in WO 02/40792, EP 0 775 741 and WO 01/94520, which are incorporated herein by reference.

According to a second aspect, the invention relates to the use of isopulegol or of the household product as defined according to the invention, as an agent for delivering a perceived cooling sensation in the air.

According to a third aspect, the invention provides a method of delivering a perceived cooling sensation in the air which comprises dispersing isopulegol into the air, or implementing the household product as defined according to the invention. The isopulegol can be dispersed or the household product can be implemented by any of the sprayers, articles and devices described herein, or by any other suitable device, or in any other suitable manner. The isopulegol can be dispersed or the household product can be implemented in the form of spray droplets.

Finally, the invention provides a method of delivering freshening and/or cooling sensation through the air which comprises implementing an air freshener dispenser device, a floor cleaner, a kitchen or bathroom surface cleaner, a toilet rim block or a toilet cistern block, as defined according to the invention.

In addition to the above provisions, the invention also comprises other provisions which will emerge from the remainder of the description which follows.

Example 1

Formulation of Fragrance A

An orange fragrance suitable for use in hard surface cleaning products and having the composition shown in Table 2 was prepared. The amounts are in % by weight.

TABLE 2

| fragrance A | | |
|---|---|---|
| Ingredients | CAS number | % by weight |
| Orange oil (California type) | 8028-48-6 | 55.99 |
| Lemon oil (Italian type) | 8008-56-8 | 20.47 |
| Grapefruit oil | 8016-20-4 | 20.47 |
| Allyl heptanoate | 142-19-8 | 0.31 |
| Decanal | 112-31-2 | 0.41 |
| Linalool | 78-70-6 | 2.35 |
| Total: | | 100.00 |

Example 2

Formulation of Fragrance B

A lime-type fragrance suitable for use in an electric air freshening device and having the composition shown in Table 3 was prepared. The amounts are in % by weight.

TABLE 3 fragrance B

| Ingredients | CAS number | % by weight |
| --- | --- | --- |
| Dipropylene glycol | 25265-71-8 | 37.60 |
| Allyl cyclohexyl propionate | 2705-87-5 | 0.81 |
| Calone 1951 | 28940-11-6 | 0.05 |
| Lemon oil | 8008-56-8 | 15.35 |
| Orange oil (Brazilian type) | 8028-48-6 | 10.87 |
| Linalool | 78-70-6 | 6.79 |
| Verdox | 88-41-5 | 5.43 |
| Citronellol | 106-22-9 | 4.07 |
| Terpinyl acetate | 80-26-2 | 2.72 |
| Linalyl acetate | 115-95-7 | 5.43 |
| Benzyl acetate | 140-11-4 | 2.72 |
| Hexyl acetate | 142-92-7 | 2.04 |
| Styrallyl acetate | 93-92-5 | 2.04 |
| Terpineol 900 alpha | 98-55-5 | 1.36 |
| Dihydromyrcenol | 18479-58-8 | 1.36 |
| Florol (registered trademark) | 63500-71-01 | 1.36 |
| Total | | 100.00 |

Example 3

Formulation of Fragrance C

An olfactive-type floral/aromatic fragrance suitable for use in any of the applications mentioned in the present disclosure and having the composition shown in Table 4 was prepared. The amounts are in % by weight.

TABLE 4 fragrance C

| Ingredients | CAS number | % by weight |
| --- | --- | --- |
| Dipropylene glycol | 25265-71-8 | 37.60 |
| Ambroxan | 6790-58-5 | 0.12 |
| Anisic aldehyde | 123-11-5 | 3.66 |
| Bacdanol | 28219-61-6 | 1.83 |
| Benzyl acetate | 140-11-4 | 1.83 |
| Benzyl salicylate | 118-58-1 | 2.44 |
| Cinnamon leaf oil | 8015-91-6 | 0.12 |
| Citronellol 950 | 106-22-9 | 2.44 |
| Ethyl vanilin | 121-32-4 | 2.44 |
| Hedione | 24851-98-7 | 2.44 |
| Hexyl cinnamic aldehyde | 101-86-0 | 3.66 |
| Cis-3-hexen-1-ol | 928-96-1 | 0.12 |
| Isoraldeine 70 | 1335-46-2 | 2.44 |
| Linalool | 78-70-6 | 6.10 |
| Musk T | 105-95-3 | 4.88 |
| Gamma nonalactone | 104-61-0 | 1.46 |
| Iso super E | 54464-57-2 | 7.32 |
| Vanilin | 121-33-5 | 3.05 |
| Vertenex | 32210-23-4 | 3.66 |
| Total | | 100.00 |

Example 4

Cooling Sensation Comparative Test

A panel of 23 subjects was selected to take part in a comparison test. The fragrance compositions according to Examples 2 and 3 were respectively compared to the same compositions, to which 5 wt % of isopulegol were added. The subjects smelt each fragrance composition from a glass jar a comfortable distance from the nose so that they could easily perceive the fragrance, and then had to decide which composition gave a cooler perceived sensation. The results are gathered in Table 5 as the % of the subjects who decided in favor of a given composition.

TABLE 5

| Fragrances | Fragrance oil | Fragrance oil + 5 wt % isopulegol |
| --- | --- | --- |
| Fragrance B | 42 | 58 |
| Fragrance C | 37 | 63 |

It can be seen from the above results that the fragrance compositions containing isopulegol gave a significantly cooler perceived sensation in the air.

Example 5

Olfactive Intensity Comparative Test

Identical fragrance compositions to those tested in Example 4 were tested for perceived olfactive intensity. In this experiment, a panel of 23 subjects scored the intensity of each composition on a scale of 0 (not detectable) to 100 (extremely strong). The results are gathered in Table 6 as the average score given to each composition.

TABLE 6

| Fragrance | Fragrance oil | Fragrance oil + 5 wt % isopulegol |
| --- | --- | --- |
| Fragrance B | 71.6 | 77.3 |
| Fragrance C | 62.3 | 59.3 |

The differences between the fragrance compositions with and without isopulegol are not statistically significant at the 95% confidence interval. These results show that the addition of isopulegol does not impact the perceived intensity of otherwise intense perfumes.

Example 6

Olfactory Event-Related Potentials (OERP) Experiment

The orange fragrance composition of Example 1 (fragrance A) was compared to the same composition to which 5 wt% isopulegol was added.

For the test, an olfactometer (Burghart OM8b) was programmed to present 90 stimulation blocks in succession. Each block contained five stimuli, three identical stimuli of fragrance A in humidified thermostatted air (stimulus H), then a stimulus of the orange fragrance composition containing isopulegol also in humidified thermostatted (stimulus D), and finally a stimulus of fragrance A. Control blocks each contained five identical stimuli of fragrance A.

Thus, the presentation sequence for a test block is:

H1, H2, H3, D, H5 while for a control block the sequence is:

H1, H2, H3, H4, H5

Presentations of test blocks and control blocks were randomly repeated for a total of 90 presentations. Periodically there was a break in testing while subjects answered a questionnaire about the fragrance compositions. The inter-stimulus interval lasted four seconds. Every stimulus block was followed by a rating period that lasted for about 20 seconds.

The stimuli were created in the olfactometer as follows:

i) Stimuli H were created with air saturated with fragrance A making up 40% of the presented air at an air flow of 2.8 litres per min (l/min) with the remaining 60% being air at a flow rate of 4.2 l/min.

ii) Stimulus D was created with air saturated with fragrance A making up 40% of the presented air, with 30% being air saturated with isopulegol at an air flow of 2.1 l/min and the remaining 30% being air at an air flow of 2.1 l/min.

The panel was comprised of 23 subjects (9 males and 14 females) with an age range of 21-35 years. All subjects had been screened by a series of tests to ensure normal olfactive function. The panel scored the intensity of each stimulus in the same manner as Example 5.

The average panel scores are gathered in Table 7 below.

TABLE 7

| Stimulus | Fragrance A (Control) | Stimulus | Fragrance A + isopulegol |
|---|---|---|---|
| H1 | 48.4 | H1 | 48.5 |
| H2 | 49.4 | H2 | 50.0 |
| H3 | 51.0 | H3 | 52.0 |
| H4 | 53.2 | D | 62.9 |
| H5 | 52.5 | H5 | 56.9 |

Responses to the 5 stimuli presentations labelled H1, H2, H3, H4 or D, H5 were only significantly different when isopulegol is added to fragrance A at presentation D (F[4;76]=12.4; p<0.001). There is no significant change for the orange fragrance control sample (F[4;76]=1.32; p=0.27).

During the same experiment olfactory-related electrophysiological measurements were recorded. ElectroEncephaloGraphy (EEG) (0.2-30 Hz band pass) was recorded from 5 positions (Fz, Cz, Pz, C3, C4) of the 10/20 system referenced to linked earlobes (A1+A2). Vertical eye movements were registered from an additional site (Fp2, referenced to A1+A2). All single responses contaminated by eye blinks were discarded before averaging. For the OERP base-to-peak amplitudes (A-N1, A-P2), peak-to-peak amplitudes (A-N1P2), and latencies (in relation to stimulus onset; T-N1, T-P2) were measured.

ERP peak-to-peak amplitudes N1P2 at recording position Cz, Fz and Pz were recorded and the results are respectively summarised in Tables 8, 9 and 10 below. For the control sample (fragrance A) H4 is identical to any of H, H2, H3 or H5 and for the test sample D is (fragrance A+isopulegol).

TABLE 8

| Stimulus | Fragrance A (Control) | Stimulus | Fragrance A + isopulegol |
|---|---|---|---|
| H1 | 4.6 | H1 | 3.9 |
| H2 | 4.2 | H2 | 3.6 |
| H3 | 3.9 | H3 | 3.0 |
| H4 | 4.8 | D | 9.0 |
| H5 | 4.1 | H5 | 5.5 |

TABLE 9

| Stimulus | Fragrance A (Control) | Stimulus | Fragrance A + isopulegol |
|---|---|---|---|
| H1 | 3.9 | H1 | 3.1 |
| H2 | 3.4 | H2 | 2.9 |
| H3 | 3.1 | H3 | 2.2 |
| H4 | 4.0 | D | 7.0 |
| H5 | 3.2 | H5 | 4.4 |

TABLE 10

| Stimulus | Fragrance A (Control) | Stimulus | Fragrance A + isopulegol |
|---|---|---|---|
| H1 | 4.4 | H1 | 4.3 |
| H2 | 4.5 | H2 | 3.6 |
| H3 | 3.8 | H3 | 3.0 |
| H4 | 4.5 | D | 7.8 |
| H5 | 3.4 | H5 | 5.0 |

For ERP peak-to-peak amplitudes N1P2 at recording positions Cz, Fz and Pz responses to the 5 stimuli were significantly different for the test sample (fragrance A+isopulegol) (F[4;76]=12.4; p<0.001), but not for fragrance A alone (control) (F[4;76]=1.32; p=0.27). Similar findings were obtained for amplitude P2 ((fragrance A+isopulegol) (F[4;76]=4.54; p=0.002; fragrance A alone (control) (F[4;76]=0.66; p=0.62).

Figure 1:
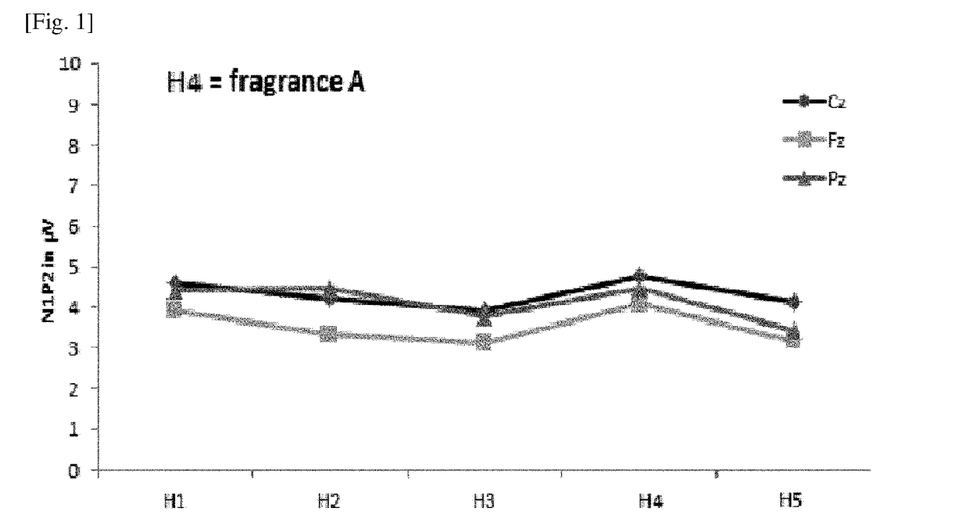
FIG. 1 represents the results of an ElectroEncephaloGraphy (EEG) experiment in subjects stimulated with an orange fragrance.
Figure 2:
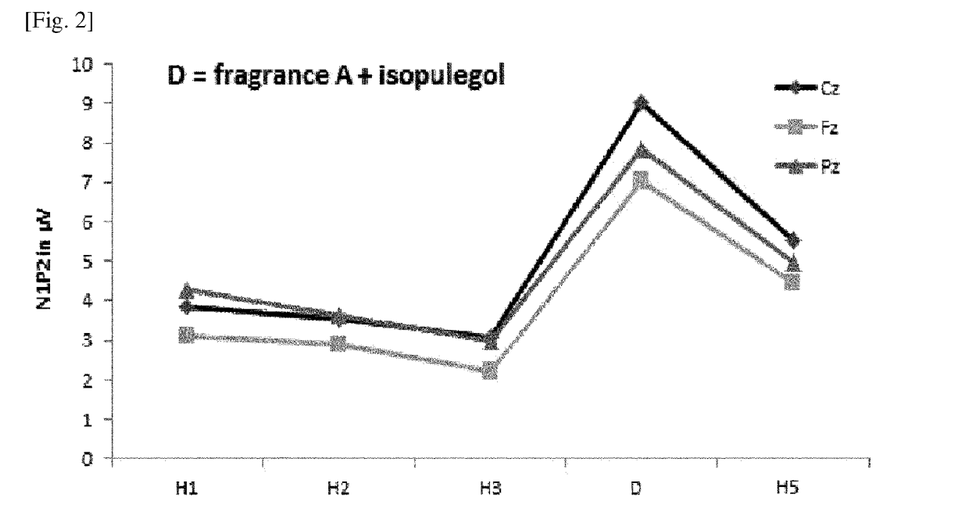
FIG. 2 represents the results of an ElectroEncephaloGraphy (EEG) experiment in subjects stimulated with the same orange fragrance of FIG. 1 to which isopulegol was added.

The effect of isopulegol is also shown in FIGS. 1 and 2 in which a stimulus with fragrance A (orange fragrance) to which isopulegol (Coolact (registered trademark) P) has been added, results in a significant increase in amplitude N1P2 at recording positions Cz, Fz and Pz compared to a stimulus with fragrance A alone.

Example 7

Comparison of Sensations Between Isopulegol and Menthoxypropanediol

A panel of 84 subjects was selected to take part in a comparative test between isopulegol (available as Coolact (registered trademark) P) and menthoxypropanediol (CAS 87061-04-9, available as Coolact (registered trademark) 10), both known for their cooling effect on skin.

The samples of isopulegol and menthoxypropanediol were prepared by dilution to 3% in Triethyl Citrate (TEC).

Panelists also had to score whether they perceived a cool sensation in the nose, on a scale of +100 (very cool) to −100 (very hot) with 0 (neutral) on the middle of the scale.

The ANOVA test and Student's t-test both showed that the subjects of the panel felt an improved cooling perception for isopulegol compared to menthoxypropanediol. These results are statistically significant (ANOVA: F ratio=5.69; p<0.05; t-test: alpha=0.05).

Example 8

TRPM8 Activation of Isopulegol and Menthoxypropanediol

TRPM8 is a member of the Transient Receptor Potential (TRP) family of cation channels and is activated by cooling. It is sometimes referred to as "the cold and menthol receptor". Whether or not isopulegol and menthoxypropanediol activate TRPM8 has been determined by the method described below.

HEK-293 (Human Embryonic Kidney) cells stably transfected with human TRPM8 were grown in a culture medium of EMEM (minimum Essential Medium Eagle) with Earl's salts balanced salt solution (Lonza catalogue No BE12-125F), 5 mL of 200 mM Ultraglutamine 1 (Lonza Catalogue No BE17-605E/U1), 5 mL of 100× Penicillin/Streptomycin (Lonza Catalogue No DE17-602E) 50 mL of Fetal bovine serum (Euroclone Cat No ECS0180L) 2 mL of 100 mg/mL Genticin sulphate (G418 sulphate InvivoGen CatAnt-gn-5).

10,000 cells/well were seeded in a 384 MTP in complete medium. Then after 24 h the culture medium was manually removed. The cells were loaded with 20 μL/well of 0.5× Fluo-8 NW dye in standard Tyrode's buffer (Screen Quest™

Fluo-8 No wash Calcium assay kit supplied by AAT Bioquest catalogue No 26316) The plate was incubated for 1 h at room temperature in the dark. 10 µL/well of test compounds and controls were injected with the FLIPR$^{TETRA}$ (Molecular Devices) and the emitted fluorescence signal was recorded at 520 nm for 3 min. The compound multiwall plate contained the samples at 8 different doses in quadruplicate data points. The dose response of the samples were performed starting from 100 mM concentration in 100% DMSO with a serial dilution of 1:2 and then diluted in assay buffer at the final concentration of 100 µM, 50 µM, 25 µM, 12.5 µM, 6 µM, 3 µM, 1.5 µM, and 0.7 µM.

In the compound plate was also present a dose response of the reference agonist N ethyl-p-menthane-3-carboxamide (WS3) at 8 concentrations and in duplicate. This reference control dosed as 16 wells (duplicates for each concentration) of reference agonist at $EC_{100}$ correspond to the MAX signal response (100% activity). There were also 16 wells of blanks i.e. assay buffer without either a test sample or reference agonist which correspond to the MIN signal response (0% activity). MAX and MIN controls are used for data analysis (RZ' calculation) and normalization of compound activity.

For data analysis the response value is calculated as the maximum signal of the kinetic trace after the injection minus the median of the points before injection and multiplied by the normalization factor (NF). The normalisation factor is the baseline mean of all wells in the plate divided by the baseline of a specific well.

The agonistic effect is expressed as a percentage of activity, with 100% activity being a result in which the response value of the test sample wells reaches a level identical to the one of the MAX controls (Max Signal wells correspond to reference agonist $EC_{100}$) and 0% activity being a result in which the response value of the test sample wells reaches a level identical to the one of the MIN controls (Min Signal wells corresponding to assay buffer).

To calculate the % Activity of the test sample the response value was normalized versus MAX signal controls and MIN Signal controls to obtain Activity % according to the following formula.

$$\text{Activity \%} = 100 * \left( \frac{x - \langle MIN \rangle}{\langle MAX \rangle - \langle MIN \rangle} \right) \quad \text{[Math. 1]}$$

The $EC_{50}$ of the test samples was then calculated using a curve fitting program available within the data analysis software. The following results were obtained.

WS3 (reference): $EC_{50}=6.0\times10^{-6}$ M

Isopulegol (Coolact (registered trademark) P): $EC_{50}=1.10\times10^{4}$ M

Menthoxypropanediol: $EC_{50}=7.7\times10^{-6}$ M

It can be seen that both isopulegol and menthoxypropanediol activate TRPM8. Although the $EC_{50}$ for isopulegol is less than that of menthoxypropanediol the former nevertheless provided an improved cooling perception. These results, taken in combination with those of Example 7, show that there is no direct relationship between activation of the TRPM8 receptor and perceived cooling sensation in the air (i.e. the stronger agonist is not necessarily the better in terms of perceived cooling sensation).

While the invention has been described in detail and with reference to specific embodiments thereof, it will be apparent to one skilled in the art that various changes and modifications can be made therein without departing from the spirit and scope thereof. This application is based on European Patent Application No. 16 305 215.2 filed on Feb. 24, 2016, the entire subject matter of which is incorporated herein by reference.

INDUSTRIAL APPLICABILITY

In the present invention, it is possible to deliver a perceived cooling sensation in the air, but without the product formulation per se coming into direct contact with the skin or mucous membranes of the subject nor of the product needing to be in close proximity to the nose.

The invention claimed is:

1. A household product comprising a fragrance composition, wherein the fragrance composition consists of:
   from about 0.2 to less than 10% by weight of isopulegol, based on the total weight of the fragrance composition,
   a perfume ingredient selected from the group consisting of $C_8$-$C_{18}$ hydrocarbons; $C_2$-$C_{18}$ aliphatic alcohols; $C_2$-$C_{18}$ aliphatic aldehydes and their acetals; $C_3$-$C_{18}$ aliphatic ketones and oximes thereof; $C_2$-$C_{18}$ aliphatic sulphur-containing compounds; $C_2$-$C_{18}$ aliphatic nitrile-containing compounds; $C_2$-$C_{18}$ aliphatic carboxylic acids and esters thereof; $C_4$-$C_{18}$ acyclic terpene alcohols; $C_4$-$C_{18}$ acyclic terpene aldehydes and ketones; $C_4$-$C_{18}$ cyclic terpene alcohols; $C_4$-$C_{18}$ cyclic terpene aldehydes and ketones; $C_4$-$C_{18}$ cyclic alcohols; $C_4$-$C_{18}$ cycloaliphatic alcohols; $C_4$-$C_{18}$ cyclic and cycloaliphatic ethers; $C_4$-$C_{18}$ cyclic ketones; $C_4$-$C_{18}$ cycloaliphatic aldehydes; $C_4$-$C_{18}$ cycloaliphatic ketones; $C_4$-$C_{18}$ esters of cyclic alcohols; $C_4$-$C_{18}$ esters of cycloaliphatic carboxylic acids; $C_4$-$C_{18}$ aromatic hydrocarbons; $C_4$-$C_{18}$ araliphatic alcohols; $C_4$-$C_{18}$ esters of araliphatic alcohols and $C_4$-$C_{18}$ aliphatic carboxylic acids; $C_2$-$C_{18}$ araliphatic ethers; $C_4$-$C_{18}$ aromatic and araliphatic aldehydes; $C_4$-$C_{18}$ aromatic and araliphatic ketones; $C_4$-$C_{18}$ nitrogen-containing aromatic compounds; phenols, phenyl ethers and phenyl esters; $C_4$-$C_{12}$ heterocyclic compounds; $C_4$-$C_{18}$ lactones; $C_4$-$C_{18}$ aromatic and araliphatic carboxylic acids and esters thereof selected from the group consisting of phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl 2,4-dihydroxy-3,6-dimethylbenzoate, ethyl 3-phenylglycidate, ethyl 3-methyl-3-phenylglycidate; and mixture thereof,
   one or more support materials selected from a solvent or a UV stabilizer, wherein the solvent is selected from the group consisting of hydrocarbons; ethers; benzyl benzoate; isopropyl myristate; dialkyl adipates; dialkyl succinates; dialkyl glutarates; citrate esters; soybean methyl ester; diethyl phthalate; diethylene glycol monoethyl ether; 3-methoxy-3-methyl-1-butanol; dipropylene glycol; and isopropylidene glycerol; and wherein the UV stabilizer is selected from the group consisting of butyl methoxy dibenzoyl methane; bis ethylhexyloxyphenolmethoxyphenyl triazine; [bis(2,4-dihydroxyphenyl)-methanone], octyl methoxycinnamate and benzophenone 3, and
   one or more cooling agents selected from the group consisting of: menthol (CAS 89-78-1), menthone (CAS 14073-97-3), menthyl acetate (CAS 79-20-9), menthyl lactate (CAS 547-64-8), camphor (CAS 76-22-2), 1,4-cineole (CAS 470-82-6), p-menthane-3,8-diol (CAS 42822-86-6), menthoxypropanediol (CAS 87061-04-9), menthone glycerin acetal (CAS 63187-91-7), 2-isopropyl-5-methylcyclohexyl-3-hydroxybutanoate (CAS 108766-16-1), N-ethyl-5-methyl-2-(1-methylethyl)cyclohexanecarboxamide (CAS 39711-79-0), N,2,3-trimethyl-2-propan-2-ylbutanamide (CAS 51115-67-4), (3S,3aR,3bR,4S,7R,7aR)-3,7-dimethyl-4-(propan-2-yl)octahydro-1H-cyclopenta[1,3]cyclopropa[1,2]benzen-3-ol (CAS 23445-02-5), spearmint oil (CAS 8008-79-5) and peppermint oil (CAS 8006-90-4).

2. The household product of claim 1, wherein the isopulegol is contained from about 0.2 to about 5% by weight based on the total weight of the fragrance composition.

3. The household product of claim 1, wherein the isopulegol is (-)-isopulegol.

4. The household product of claim 1, wherein the one or more cooling agents are contained from about 0.1 to about 10% by weight, based on the total weight of the fragrance composition.

5. The household product of claim 1, wherein the household product is selected from the group consisting of an air freshener dispenser device, a kitchen surface cleaner, a bathroom surface cleaner, a floor cleaner, a carpet cleaner, a toilet rim block, and a toilet cistern block.

6. The household product of claim 1, wherein the UV stabilizer is selected from the group consisting of butyl methoxy dibenzoyl methane; bis ethylhexyloxyphenolmethoxyphenyl triazine; and bis(2,4-dihydroxyphenyl)-methanone.

7. A method for delivering a perceived cooling sensation in the air which comprises dispersing isopulegol into the air without isopulegol per se coming into direct contact with the skin, or implementing a household product comprising a fragrance composition, without isopulegol per se coming into direct contact with the skin, wherein the fragrance composition consists of:
from about 0.2 to less than 10% by weight of isopulegol, based on the total weight of the fragrance composition,
a perfume ingredient selected from the group consisting of $C_8$-$C_{18}$ hydrocarbons; $C_2$-$C_{18}$ aliphatic alcohols; $C_2$-$C_{18}$ aliphatic aldehydes and their acetals; $C_3$-$C_{18}$ aliphatic ketones and oximes thereof; $C_2$-$C_{18}$ aliphatic sulphur-containing compounds; $C_2$-$C_{18}$ aliphatic nitrile-containing compounds; $C_2$-$C_{18}$ aliphatic carboxylic acids and esters thereof; $C_4$-$C_{18}$ acyclic terpene alcohols; $C_4$-$C_{18}$ acyclic terpene aldehydes and ketones; $C_4$-$C_{18}$ cyclic terpene alcohols; $C_4$-$C_{18}$ cyclic terpene aldehydes and ketones; $C_4$-$C_{18}$ cyclic alcohols; $C_4$-$C_{18}$ cycloaliphatic alcohols; $C_4$-$C_{18}$ cyclic and cycloaliphatic ethers; $C_4$-$C_{18}$ cyclic ketones; $C_4$-$C_{18}$ cycloaliphatic aldehydes; $C_4$-$C_{18}$ cycloaliphatic ketones; $C_4$-$C_{18}$ esters of cyclic alcohols; $C_4$-$C_{18}$ esters of cycloaliphatic carboxylic acids; $C_4$-$C_{18}$ aromatic hydrocarbons; $C_4$-$C_{18}$ araliphatic alcohols; $C_4$-$C_{18}$ esters of araliphatic alcohols and $C_4$-$C_{18}$ aliphatic carboxylic acids $C_2$-$C_{18}$ araliphatic ethers; $C_4$-$C_{18}$ aromatic and araliphatic aldehydes; $C_4$-$C_{18}$ aromatic and araliphatic ketones; $C_4$-$C_{18}$ nitrogen-containing aromatic compounds; phenols, phenyl ethers and phenyl esters; $C_4$-$C_{12}$ heterocyclic compounds; $C_4$-$C_{18}$ lactones; $C_4$-$C_{18}$ aromatic and araliphatic carboxylic acids and esters thereof selected from the group consisting of phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl 2,4-dihydroxy-3,6-dimethylbenzoate, ethyl 3-phenylglycidate, ethyl 3-methyl-3-phenylglycidate; and mixture thereof,
one or more solvents selected from the group consisting of hydrocarbons; ethers; benzyl benzoate; isopropyl myristate; dialkyl adipates; dialkyl succinates; dialkyl glutarates; citrate esters; soybean methyl ester; diethyl phthalate; diethylene glycol monoethyl ether; 3-methoxy-3-methyl-1-butanol; dipropylene glycol; and isopropylidene glycerol,
one or more cooling agents selected from the group consisting of: menthol (CAS 89-78-1), menthone (CAS 14073-97-3), menthyl acetate (CAS 79-20-9), menthyl lactate (CAS 547-64-8), camphor (CAS 76-22-2), 1,4-cineole (CAS 470-82-6), p-menthane-3,8-diol (CAS 42822-86-6), menthoxypropanediol (CAS 87061-04-9), menthone glycerin acetal (CAS 63187-91-7), 2-isopropyl-5-methylcyclohexyl-3-hydroxybutanoate (CAS 108766-16-1), N-ethyl -5-methyl-2-(1-methylethyl)cyclohexanecarboxamide (CAS 39711-79-0), N,2,3-trimethyl-2-propan-2-ylbutanamide (CAS 51115-67-4), (3S,3aR,3bR,4S,7R,7aR)-3,7-dimethyl-4-(propan-2-yl)octahydro-1H-cyclopenta[1,3]cyclopropa[1,2]benzen-3-ol (CAS 23445-02-5), spearmint oil (CAS 8008-79-5) and peppermint oil (CAS 8006-90-4).

8. The method of claim 7, wherein the isopulegol is contained from about 0.2 to about 5% by weight based on the total weight of the fragrance composition.

9. The method of claim 7, wherein the isopulegol is (-)-isopulegol.

10. The method of claim 7, wherein the one or more cooling agents are contained from about 0.1 to about 10% by weight, based on the total weight of the fragrance composition.

11. The method of claim 7, wherein the household product is an air freshener dispenser device.

12. The method of claim 7, wherein the household product is a toilet rim block or a toilet cistern block.

13. The method of claim 7, wherein the household product is selected from the group consisting of an air freshener dispenser device, a kitchen surface cleaner, a bathroom surface cleaner, a floor cleaner, a carpet cleaner, a toilet rim block, and a toilet cistern block.

14. A method for delivering a perceived cooling sensation in the air which comprises dispersing isopulegol into the air without isopulegol per se coming into direct contact with the skin, or implementing a household product comprising a fragrance composition, without isopulegol per se coming into direct contact with the skin,
wherein isopulegol acts by stimulating the receptors of the trigeminal nerve, and
the fragrance composition consists of:
from about 0.2 to less than 10% by weight of isopulegol, based on the total weight of the fragrance composition,
a perfume ingredient selected from the group consisting of $C_8$-$C_{18}$ hydrocarbons; $C_2$-$C_{18}$ aliphatic alcohols; $C_2$-$C_{18}$ aliphatic aldehydes and their acetals; $C_3$-$C_{18}$ aliphatic ketones and oximes thereof; $C_2$-$C_{18}$ aliphatic sulphur-containing compounds; $C_2$-$C_{18}$ aliphatic nitrile-containing compounds; $C_2$-$C_{18}$ aliphatic carboxylic acids and esters thereof; $C_4$-$C_{18}$ acyclic terpene alcohols; $C_4$-$C_{18}$ acyclic terpene aldehydes and ketones; $C_4$-$C_{18}$ cyclic terpene alcohols; $C_4$-$C_{18}$ cyclic terpene aldehydes and ketones; $C_4$-$C_{18}$ cyclic alcohols; $C_4$-$C_{18}$ cycloaliphatic alcohols; $C_4$-$C_{18}$ cyclic and cycloaliphatic ethers; $C_4$-$C_{18}$ cyclic ketones; $C_4$-$C_{18}$ cycloaliphatic aldehydes; $C_4$-$C_{18}$ cycloaliphatic ketones; $C_4$-$C_{18}$ esters of cyclic alcohols; $C_4$-$C_{18}$ esters of cycloaliphatic carboxylic acids; $C_4$-$C_{18}$ aromatic hydrocarbons; $C_4$-$C_{18}$ araliphatic alcohols; $C_4$-$C_{18}$ esters of araliphatic alcohols and $C_4$-$C_{18}$ aliphatic carboxylic acids; $C_2$-$C_{18}$ araliphatic ethers; $C_4$-$C_{18}$ aromatic and araliphatic aldehydes; $C_4$-$C_{18}$ aromatic and araliphatic ketones; $C_4$-$C_{18}$ nitrogen-containing aromatic compounds; phenols, phenyl ethers and phenyl esters; $C_4$-$C_{12}$ heterocyclic compounds; $C_4$-$C_{18}$ lactones; $C_4$-$C_{18}$ aromatic and araliphatic carboxylic acids and esters thereof selected from the group consisting of phenylacetic acid, methyl benzoate, ethyl benzoate, hexyl benzoate, benzyl benzoate, methyl phenylacetate, ethyl phenylacetate, geranyl phenylacetate, phenylethyl phenylacetate, methyl cinnamate, ethyl cinnamate, benzyl cinnamate, phenylethyl cinnamate, cinnamyl cinnamate, allyl phenoxyacetate, methyl 2,4-dihydroxy-3,6-dimethylbenzoate, ethyl 3-phenylglycidate, ethyl 3-methyl-3-phenylglycidate; and mixture thereof, one or more solvents selected from the group consisting of hydrocarbons; ethers; benzyl benzoate; isopropyl myristate; dialkyl adipates; dialkyl succinates; dialkyl glutarates; citrate esters; soybean methyl ester; diethyl phthalate; diethylene glycol monoethyl ether; 3-methoxy-3-methyl-1-butanol; dipropylene glycol; and isopropylidene glycerol; and wherein the UV stabilizers is selected from the group consisting of butyl methoxy dibenzoyl methane; bis ethylhexyloxyphenolmethoxyphenyl triazine; [bis(2,4-dihydroxyphenyl)-methanone], octyl methoxycinnamate and benzophenone 3, and one or more cooling agents selected from the group consisting of: menthol (CAS 89-78-1), menthone (CAS 14073-97-3), menthyl acetate (CAS 79-20-9), menthyl lactate (CAS 547-64-8), camphor (CAS 76-22-2), 1,4-cineole (CAS 470-82-6), p-menthane-3,8-diol (CAS 42822-86-6), menthoxypropanediol (CAS 87061-04-9), menthone glycerin acetal (CAS 63187-91-7), 2-isopropyl-5-methylcyclohexyl-3-hydroxybutanoate (CAS 108766-16-1), N-ethyl-5-methyl-2-(1-methylethyl)cyclohexanecarboxamide (CAS 39711-79-0), N,2,3-trimethyl-2-propan-2-ylbutanamide (CAS 51115-67-4), (3S,3aR,3bR,4S,7R,7aR)-3,7-dimethyl-4-(propan-2-yl)octahydro-1H-cyclopenta[1,3]cyclopropa[1,2]benzen-3-ol (CAS 23445-02-5), spearmint oil (CAS 8008-79-5) and peppermint oil (CAS 8006-90-4).

* * * * *